(12) United States Patent
Lennon et al.

(10) Patent No.: US 6,734,424 B2
(45) Date of Patent: May 11, 2004

(54) METHOD FOR MICRODISPENSING OF FLUIDS FROM A PIPETTE

(75) Inventors: John Lennon, Blacksburg, VA (US); Taraneh Norouzi, Potomac, MD (US)

(73) Assignee: Large Scale Proteomics Corporation, Vacaville, CA (US)

( * ) Notice: Subject to any disclaimer, the term of this patent is extended or adjusted under 35 U.S.C. 154(b) by 54 days.

(21) Appl. No.: 10/146,134

(22) Filed: May 16, 2002

(65) Prior Publication Data

US 2003/0213905 A1 Nov. 20, 2003

(51) Int. Cl.⁷ .......................... B01D 59/44; G01N 21/00
(52) U.S. Cl. ...................... 250/288; 73/864.22
(58) Field of Search ................ 250/288, 282, 250/281; 73/864.01, 864.11, 864.21, 864.53, 864.72, 864.61, 864.81, 864.71, 864.87, 23.41, 864.22; 422/100, 102; 141/206; 222/426

(56) References Cited

U.S. PATENT DOCUMENTS

| | | | |
|---|---|---|---|
| 4,598,596 A | * | 7/1986 | Wiseman et al. ........ 73/864.22 |
| 4,988,618 A | | 1/1991 | Li et al. |
| 5,118,937 A | | 6/1992 | Hillenkamp et al. |
| 5,312,757 A | * | 5/1994 | Matsuyama et al. ........ 422/100 |
| 5,468,453 A | | 11/1995 | Holt et al. |
| 5,770,860 A | | 6/1998 | Franzen |
| 5,841,136 A | | 11/1998 | Holle et al. |
| 5,854,486 A | | 12/1998 | Dreyfus |
| 6,265,716 B1 | | 7/2001 | Hunter et al. |
| 6,302,159 B1 | | 10/2001 | Ryan et al. |
| 2002/0182117 A1 | * | 12/2002 | Coassin et al. ............. 422/100 |

* cited by examiner

*Primary Examiner*—John R. Lee
*Assistant Examiner*—James P. Hughes
(74) *Attorney, Agent, or Firm*—John E. Tarcza; John C. Robbins (57) ABSTRACT

An automated pipetting apparatus and method for forming sample spots on a support include a pipette. A robotic assembly moves a sample container, such as a multiwell microtiter plate, and the support to the pipette for receiving and dispensing liquid samples. The pipette draws a predetermined volume of the liquid sample from the sample container into the axial passage of the pipette and forms a pocket of a gaseous material above and forms a barrier material below the volume of the liquid sample. The liquid sample is drawn into the pipette a distance sufficient to form a space between the liquid sample and the outlet of the pipette and to contain the liquid sample completely within the pipette. The volume of the barrier material, which is typically air or other fluid, separates the liquid sample a suitable distance from the outlet end of the pipette to prevent the liquid sample from flowing outward under gravity and being drawn along the outer surfaces of the pipette by the surface tension of the liquid, thereby preventing or inhibiting evaporation and preventing deposits from forming on the outer surface of the pipette. The pipette dispenses the liquid sample with sufficient force so that substantially the entire volume of the liquid sample is dispensed from the pipette directly onto the support. The support can be, for example, a sample plate of a MALDI mass spectrometer. The pipette deposits the liquid samples to form sample spots on the sample plate for analysis by the mass spectrometer.

41 Claims, 8 Drawing Sheets

METHOD FOR MICRODISPENSING OF FLUIDS FROM A PIPETTE

FIELD OF THE INVENTION

The present invention is directed to a method and apparatus for dispensing fluids from a pipette, and particularly for dispensing small volumes of liquids from a micropipette. The invention is also directed to a method and apparatus for capturing and dispensing a predetermined volume of a liquid sample containing volatile components using a micropipette.

BACKGROUND OF THE INVENTION

Chemical analysis often requires transferring samples between vessels or containers and adding various reagents to the samples. In recent years, various devices have been developed for the automation of pipettes for transferring the sample from storage vessels to various reaction containers. Automated pipetting devices are particularly desirable where large numbers of samples are being handled. Automated pipetting devices have the advantage of accurately transferring uniform and consistent volumes of various samples to a desired location.

One analytical device that has gained widespread use in recent years is mass spectrometry. In particular, matrix-assisted laser desorption/ionization (MALDI) mass spectrometry is commonly used in the analysis of analytes and other biological materials. The ionization of biomolecular samples using a MALDI mass spectrometer and particularly time of flight mass spectrometers apply a sample to the surface of a solid support which is then introduced into the vacuum system of the mass spectrometer. The solid support typically contains a large number of samples arranged in an array. The sample support is positioned in the mass spectrometer so that the samples are positioned in the focus point of the laser.

The support plate is loaded with the samples to be analyzed by applying small drops of a solution containing the sample. The solution generally includes a volatile or low boiling solvent or carrier, which evaporates quickly to produce a sample spot. Typically, a matrix substance is added to the solution for the MALDI mass spectrometer analysis. The matrix encapsulates the sample material as the solvent dries. In other methods, a matrix layer is first applied to the support and dried. Thereafter, the sample is then applied onto the dried matrix material. A solvent can be applied to disperse the sample in the matrix.

Automation of the sample loading onto the support plate provides speed and accuracy to the process. In particular, automation enables the analysis of thousands of samples per day that is not available by manually handling of the samples. In addition, higher densities of samples can be loaded onto the MALDI sample plate by automation than can be obtained by manual manipulation of the samples. One example of an automated device for loading samples onto a support for a mass spectrometer is disclosed in U.S. Pat. No. 5,770,860 to Franzen.

Biological samples are often stored and processed in micro-titer plates having a large number of wells. Each sample well of the micro-titer plate contains a sample to be analyzed. Micro-titer plates generally have at least 96 sample wells arranged in a grid. Micro-titer plates having 384 wells and 1536 wells are also known.

MALDI mass spectrometry often forms the samples on a support using a volatile solvent, which can evaporate quickly. When a pipette is used to transfer the sample from a storage vial to the support plate, an amount of the sample is drawn into the pipette and the pipette is moved to a location above the support plate. A disadvantage of this pipetting method is that droplets of the liquid sample collect on the outer surface of the pipette. In addition, the, liquid sample is drawn from the inside of the pipette up along the outer surface by the surface tension of the liquid sample. The evaporation of the volatile solvent interferes with the ability to dispense predetermined amounts of the solvent from the pipette into the plate. In some instances, the volatile solvents can evaporate from the liquid and form crystals on the outside of the pipette. The buildup of the dried sample and matrix material on the outer surface of the pipette can interfere with dispensing of the sample onto the support plate and can result in cross contamination of samples as the pipette is transferred between sample wells.

Although the prior methods have been suitable for their intended purpose, they have certain disadvantages due to the nature of the solvent and carrier systems and the support plates. Accordingly, there is a continuing need in the industry for an improved method for handling biological samples.

SUMMARY OF THE INVENTION

The present invention is directed to a method and apparatus for dispensing fluids from a pipette. More particularly, the invention is directed to a method and apparatus for dispensing a predetermined amount of liquid sample using a micropipette where the liquid sample contains a volatile solvent or carrier.

Accordingly, a primary aspect of the invention is to provide a method and apparatus for loading a plurality of samples onto a support for various processes. The method and apparatus are particularly suitable for depositing a sample onto a support plate for mass spectrometry analysis.

Another aspect of the invention is to provide an automated method for transferring a large number of samples from sample containers to a support surface and for producing microarrays for various uses.

Still another aspect of the invention is to provide a method of pipetting a liquid sample containing a volatile solvent or carrier in a manner to minimize evaporation of the solvent from the pipette. Small quantities of volatile liquids can be pipetted with little or no loss of the liquid.

A further aspect of the invention is to provide a method of handling liquid samples that contain a volatile liquid component and transferring a small volume of the sample to a selected location. In one embodiment, the method transfers liquids having a volume of about 10 microliters or less.

Another aspect of the invention is to provide a method of loading a plurality of samples onto a plate for MALDI mass spectrometry, direct ionization mass spectrometry, fast atom bombardment, field desorption, and atmospheric pressure ionization.

Still another aspect of the invention is to provide a method of transferring liquid samples from the wells of a microtiter plate to a support or vessel using a micropipette with minimum evaporation or loss of the liquid and sample between the microtiter plate and the support plate.

A further aspect of the invention is to provide a method for loading liquid samples onto a support plate using a pipette or probe containing a pressure transmitting liquid for drawing a liquid sample into the pipette and dispensing the liquid sample onto the support plate.

Another aspect of the invention is to provide a method for transferring a liquid sample using a pipette containing a pressure transmitting liquid where the sample liquid is drawn into the pipette to form a bubble or volume of the liquid sample that is spaced from the end of the pipette a distance to reduce evaporation and loss of the liquid sample from the pipette.

A still further aspect of the invention is to provide a method of transporting a liquid sample using a pipette and inhibiting the formation and evaporation of droplets of the liquid sample on the outer surface of the pipette.

Another aspect of the invention is to provide a method of transporting a liquid sample in a pipette by forming an air pocket on the upstream side of a volume of the liquid sample and a volume of a barrier material on the downstream side of the volume of the liquid sample between the liquid sample and the discharge end of the pipette.

A further aspect of the invention is to provide a method of transporting a liquid sample in a pipette, where an air pocket is positioned above the liquid sample and an air pocket is provided between the liquid sample and the end of the pipette, and where the sample is discharged from the pipette with sufficient force to dispense and deposit the sample on a support plate substantially without the liquid adhering to the pipette.

The aspects of the invention are basically attained by providing a method of depositing a liquid sample onto a support. The method comprises the steps of: providing a support having a top surface for supporting a liquid sample and providing a pipette having an axial passage and an open axial end. A volume of a liquid sample is drawn through the open axial end of the pipette into the axial passage. A volume of a barrier material is drawn through the open axial end of the pipette to draw the volume of the liquid sample into the axial passage and to space the liquid sample from the axial end by the volume of the barrier material to inhibit evaporation of the liquid sample from the pipette. The pipette is positioned above a target site on the support to expel the volume of the barrier material from the pipette, and discharge the liquid sample onto the target site.

The aspects of the invention are further attained by providing a method of loading at least one biological material onto a mass spectrometer plate. The method comprises the steps of: drawing a volume of a liquid sample and drawing a volume of a barrier material into a pipette to space the volume of liquid from an outlet end of said pipette to inhibit loss of said liquid material from the pipette. The pipette is positioned over a mass spectrometer plate while retaining the volume of liquid sample completely within the pipette. The barrier material and the volume of liquid sample are discharged and the liquid sample is deposited onto a target site on the plate.

The aspects of the invention are also attained by providing a method of loading a sample onto a mass spectrometer plate. The method comprises the steps of: providing a pipette having an axial passage and an open axial end; inserting the open axial end of the pipette into a sample supply; and drawing a volume of the liquid sample into the axial passage. The open end of the pipette is removed from the liquid sample and a volume of a barrier material is drawn into the pipette through the open axial end to space the volume of liquid sample from the open axial end to inhibit evaporation of the sample. The open axial end of the pipette is positioned over a target site of a mass spectrometer plate and the barrier material and volume of liquid sample is discharged from the pipette to load the volume of liquid sample on the target site.

The aspects of the invention are further attained by providing a method of forming a sample spot on a mass spectrometer plate suitable for mass spectrometer analysis. The method comprises the steps of: loading a liquid sample containing an analyte to be analyzed onto a support plate to form a liquid sample spot and pipetting a liquid matrix forming material directly onto the sample spot. The liquid contains a volatile liquid having a vapor pressure of at least 3.5 kPa at 25° C. and a mass spectrometry matrix material. The volatile liquid is evaporated to recrystallize the matrix material and analyte.

The various aspects, advantages and other salient features of the invention will become apparent to one skilled in the art in view of the following detailed description of the invention and the annexed drawings which form a part of this original disclosure.

BRIEF DESCRIPTION OF THE DRAWINGS

The following is a brief description of the drawings, in which.

DETAILED DESCRIPTION OF THE INVENTION

The present invention is directed to a method and apparatus for capturing, transporting and dispensing fluids using a pipette or probe. The invention is also directed to a method and apparatus for capturing, transporting and dispensing a liquid sample containing a volatile component, and particularly a volatile solvent. The method and apparatus are particularly suitable for dispensing a volatile liquid solvent or carrier that evaporates quickly at ambient temperature and atmospheric pressure.

The method and apparatus of the invention are used to collect, transport and dispense small volumes of a liquid. Volatile liquids can be difficult to handle in precise amounts as a result of the evaporation. The evaporation can occur from the container and the dispensing apparatus, which can produce variations in the amount of the liquid dispensed. As used herein, the term volatile liquid refers to liquids that have a vapor pressure higher than about 3.5 kPa at 25° C. and have a rate of evaporation higher than water. The invention is particularly suitable for dispensing liquids that have a rate of evaporation where the evaporation results in a difference between the volume that is drawn into the pipette and the volume that is dispensed or variations in the concentration of a solute. The method and apparatus are particularly suitable for dispensing volatile liquids having a vapor pressure of about 7.0 kPa and above, and preferably, about 11 kPa and above at 25° C. In one embodiment, the pipetting apparatus dispenses small volumes of acetonitrile, which has a vapor pressure of about 11.8 kPa at 25° C.

The method and apparatus of the invention are suitable for withdrawing a substance from a container and dispensing the substance onto a suitable support. In the illustrated embodiments, the method and apparatus are used in connection with a mass spectrometer for depositing a solution or dispersion containing an analyte that can contain a matrix material onto a support plate for analysis. The apparatus is preferably an automated computer controlled robotic apparatus that is preprogrammed or programmable by the operator to load a large number of samples from a storage container onto a support plate in an array.

The method and apparatus are suitable for dispensing small amounts of liquids for various analytical processes. The method and apparatus can be used to produce microarrays and semi-microarrays for various purposes. The method and apparatus are particularly suitable for quantitative and qualitative analysis processes where precise volumes of reagents, solvents or samples are dispensed. In the illustrated embodiment, the apparatus is for dispensing small volumes of samples, solvents and matrix materials into a mass spectrometry plate, such as MALDI mass spectrometry and direct ionization mass spectrometry. It will be appreciated that the method and apparatus are suitable for transferring small quantities of liquids to a variety of surfaces or receptacles for a number of different uses. Other uses of the method and apparatus include microarray spotting. The microarray spotting can be for selective absorption of sample compounds, subcellular structures, bacteria and whole cells for later elution. Samples can be dispensed for analysis by various processes, such as spectrophotometric, optical, electrical and other processes. The invention is also suitable for loading microfluidic chambers, operating printing devices, and for depositing multiple layers on a surface. The method and apparatus are also suitable for transferring samples, solvents or reagents between containers, such as, for example, multiwell microtiter plates. In the embodiments described herein, the support is a mass spectrometry plate although it will be understood that the method and apparatus can be used in various other containers or supports where small volumes of the liquid are to be handled.

In the embodiment depicted in the drawings, the samples being processed are biological samples or analyte molecules that are amenable to analysis by mass spectrometry. In the illustrated embodiment, the samples are analyzed by matrix-assisted laser desorption/ionization (MALDI) time-of-flight mass spectrometry (TOF). The MALDI mass spectrometric techniques can also be used with methods other than time-of-flight, such as magnetic sector, Fourier-transform ion cyclotron resonance, quadrupole, and quadrupole ion trap.

MALDI-TOF mass spectrometry uses laser pulses that are focused on a small sample plate containing analyte molecules for the analysis. The samples, such as nucleic acids, are contained in either a solid support or a liquid matrix. The matrix typically contains a small, highly photoabsorbent material, such as small aromatic molecules. The molecules and the analyte are ionized by the laser pulse. Typically, the analyte molecules on the sample support plate are crystallized with a large molar excess of a photoabsorbing matrix material.

The laser pulse applies the energy to the matrix, which causes a microscopic ablation and ionization of the analyte molecules to produce to a gaseous plume of the analyte. It is believed that the matrix molecules carry the analyte into the plume of the gas phase and ions by the laser. The ions generated by the laser pulses are accelerated to a fixed kinetic energy by a strong electric field. The ions then pass through a vacuum in the absence of an electric field and travel at a velocity corresponding to their respective mass-to-charge ratio. The ions having the smaller mass-to-charge ratio travel through the vacuum region at a rate faster than the larger mass-to-charge ions and separate according to the size. At the end of the vacuum region, the ions collide with a detector to generate a signal corresponding to each set of ions of a particular mass-to-charge ratio.

The mass-to-charge ratio of the ion is determined from the velocity by the time-of-flight analysis. The mass of the molecule directly correlates with the time it takes to travel from the sample plate to the detector. Thus, the mass of the ion is determined from the velocity and the mass-to-charge ratio.

The MALDI-TOF mass spectrometer is suitable for the analysis of large molecules and particularly biomolecules such as nucleic acids including DNA and RNA, proteins, peptide nucleic acids and oligosaccharides. In one embodiment, a mixture of the analyte and matrix material is prepared for depositing on the MALDI plate. The mixture is prepared by dissolving the analyte in a solution containing the matrix material. Suitable solvents include, for example, ethanol, methanol, toluene, acetone, and acetonitrile. The solvents are generally volatile at ambient or room temperature and atmospheric pressure. The solvents have a low boiling point and a high vapor pressure and evaporate quickly from the container and the pipette. As discussed hereinafter in greater detail, the dispensing pipette of the invention eliminates or reduces evaporation of the solvent during the handling, transporting and dispensing of the sample. Examples of suitable matrix materials include a phenol, a hydroxyquinoline, or a hydroxynaphthalene group. In embodiments of the invention, the matrix material can be 4-nitrophenol, 8-hydroxyquinoline, nicotinic acid, 2,5-dihydroxybenzoic acid, aminobenzoic acid, pyrazinecarboxylic acid, vanillic acid, cinnamic acid, 3-nitrobenzyl alcohol, and derivatives thereof.

The mixture of the analyte and the matrix material can be deposited directly on the support plate to allow the volatile solvent to evaporate. The analyte molecules are held by the crystals of the matrix material which grow during the evaporation of the solvent.

The MALDI-TOF mass spectrometer generally includes a frame for supporting electronic and computer equipment for controlling a laser. The laser is generally aimed at a fixed location in a positioning mechanism. The positioning mechanism is operatively connected to the computer to position the sample in the line of fire of the laser. Typically, the MALDI-TOF apparatus uses a sample plate containing a plurality of samples. The sample plate is dimensioned to fit within the apparatus to support the samples during the ionization of the samples by the laser and the analysis of the samples. The sample plates preferably hold a large number of discrete samples that are spaced apart in a specifically defined array that correspond to the firing of the laser.

Figure 1:
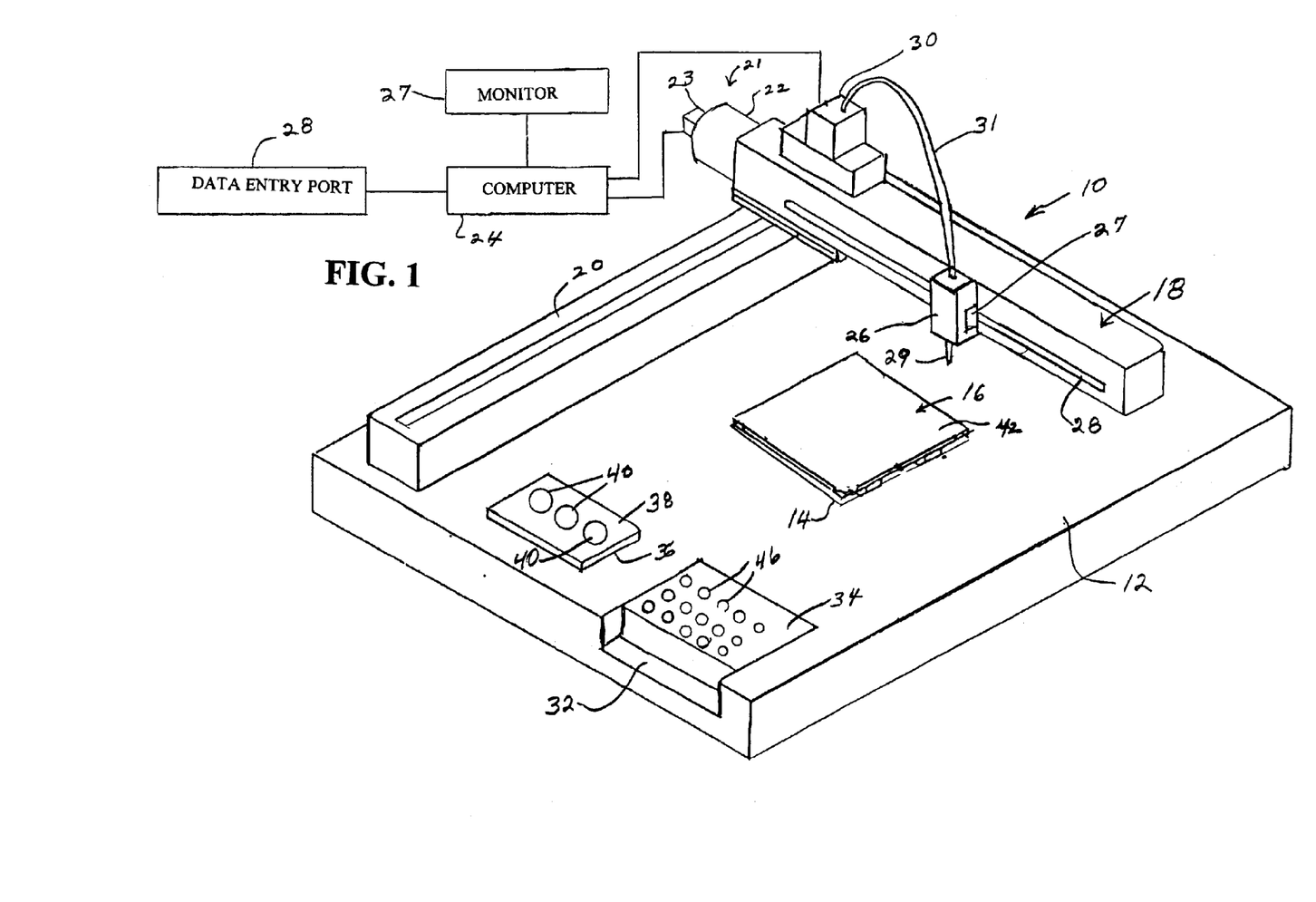
FIG. 1 is a perspective view of an automated pipetting assembly in a first embodiment of the invention.

In one embodiment, the MALDI sample plate is loaded with a plurality of samples containing an analyte using an automated pipetting apparatus. In one embodiment of the invention, the automated pipetting apparatus 10 as shown in FIG. 1 includes a base 12 having a recess 14 for receiving a sample plate 16. Recess 14 positions sample plate 16 in a fixed location during the loading process. In alternative embodiments, base 12 can have a suitable coupling member to position sample plate 16 in a selected location while loading samples onto sample plate 16.

Apparatus 10 is suitable for pipetting small and precise amounts of a liquid to a vessel or support with minimal loss of the liquid from evaporation or spilling. In one embodiment, the apparatus 10 is used to pipette small volumes of a liquid in the range of about 0.5 microliter to about 3 ml. Typically, the apparatus can pipette volumes of less than 2 ml. In other embodiments, the apparatus pipettes a volume of about 10 microliters or less. In the illustrated embodiment, the apparatus is used to pipette a volume of liquid ranging from about 0.5 to about 2.0 microliters, and typically about 0.5 to 1.5 microliters.

In the illustrated embodiment of FIG. 1, apparatus 10 includes a robotic arm 18 coupled to a stationary rail 20. Arm 18 is movable in a longitudinal direction along a track in rail 20 by a suitable drive mechanism 21. The drive mechanism 21 includes a drive motor 22 and actuator switch 23 that is operatively connected to a computer or microprocessor 24 for controlling the movement of arm 18 along the length of rail 20. An operating arm 26 is coupled to arm 18 and is movable in a longitudinal direction with respect to the longitudinal dimension of arm 18 and in a vertical direction with respect to base 12. Operating arm 26 includes a suitable drive mechanism 27 for movement along a track 28 extending the length of arm 18. The drive mechanism 27 is operatively connected to microprocessor 24 to coordinate and control the vertical and longitudinal movement of operating arm 26 with the movement of arm 18. Microprocessor 24 preferably includes a monitor 27 and data entry portion 28 such as a keyboard to enable the operator to program an actuate apparatus 10.

In the illustrated embodiment, operating arm 26 is mounted on robotic arm 18 for linear movement along X and Y coordinates with respect to base 12. In other embodiments, microprocessor 24 can be programmed to move operating arm 26 by selected polar coordinates. In alternative embodiments, the robotic arm can be an articulated robotic arm capable of moving in x, y and z coordinates or directions with respect to base 12. Preferably, the robotic arm is provided with suitable operating motors to provide the required control to load the samples onto the plate in a predetermined array or pattern as discussed hereinafter.

Operating arm 26 includes a pipette 29 extending in a downward direction toward base 12. In the illustrated embodiment, the apparatus 10 includes a single pipette 29 that reciprocates in a vertical direction to sequentially transfer liquid samples from a selected well of a vessel to sample plate 16. Pipette 29 is coupled to a pump 30 by a supply tube 31 for drawing a sample into pipette 29 and dispensing the sample onto sample plate 16. Pump 30 is operatively connected to microprocessor 24 for controlling the drawing and dispensing of the samples. Preferably, pump 30 is a dual directional pump or syringe pump that is able to produce a suction for drawing the sample into pipette 29 and to produce dispensing pressure to discharge the sample from pipette 29.

In the embodiment of FIG. 1, base 12 includes a recess 32 for receiving and supporting a microtiter plate 34. Alternatively, base 12 can include a coupling member for securing microtiter plate 34 in a fixed location while the samples are transferred to the sample plate. In other embodiments, an automated conveying system is provided to convey a microtiter plate from a storage device into position for cooperating with automated pipetting apparatus 10. The conveying device removes the microtiter plate from apparatus 10 after the samples have been transferred to the sample plate 16 and conveyed to a storage device. A second microtiter plate can then be conveyed into position for transferring the samples.

The microtiter plate can be a standard multiwell microtiter plate as known in the art for containing and storing biological samples. Typically, microtiter plate 34 is a 96 well plate. In the embodiment of FIG. 1, apparatus 10 also includes a recess 36 for receiving a container 38 having several wells 40 containing various wash solutions and reagents commonly used in preparing samples for a MALDI mass spectrometer.

Figure 2:
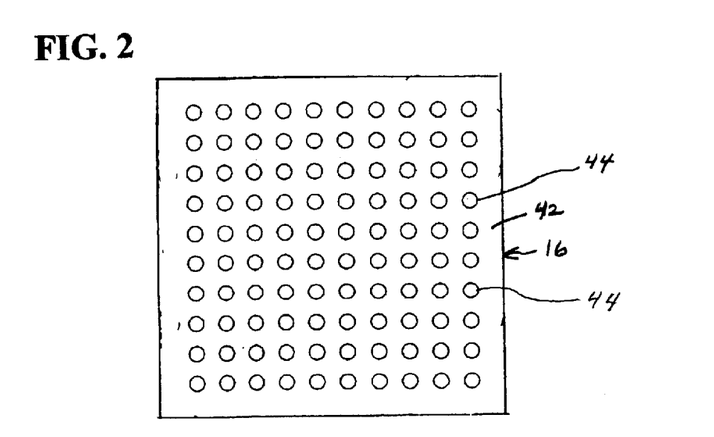
FIG. 2 is a top view of a MALDI mass spectrometry plate showing a plurality of sample sites.

Sample plate 16 as shown in FIG. 2 has a substantially flat top surface 42 for receiving the analyte samples 44. Samples 44 as shown in FIG. 2 are generally arranged in a plurality of spaced apart rows and columns, although other patterns can be used according to the requirements of the sample plate and the mass spectrometer. Samples 44 are positioned on sample plate 16 in a predetermined pattern or array according to the MALDI mass spectrometer so that the laser beam can be targeted selectively onto samples 44.

Apparatus 10 is operated by microprocessor 24 to move arm 18 and operating arm 26 to a position above a selected well 46 of microtiter plate 34. Operating arm 26 and pipette 29 are lowered to insert pipette 29 into a selected well 46. Microprocessor 24 then actuates pump 30 to withdraw a sample from the selected well 46 into pipette 29. Pipette 29 is then raised from well 46 and moved to a selected position on sample plate 16 where the sample is dispensed from pipette 29 onto top surface 42 of sample plate 16. Pipette 29 can then be moved to a cleaning station, such as at well 48, or discarded and replaced with a clean pipette for transferring another sample from microtiter plate 34 to sample plate 16.

Microprocessor 24 is typically programmed to actuate operating arm 26 and pipette 29 to remove a selected sample from each sample well 46 sequentially and deposit the sample onto sample plate 16 in a controlled and continuous sequence. Microprocessor 26 controls the timing and sequence of pipette 29 and pump 30 to deliver a predetermined volume of the sample onto sample plate 16. Preferably, microprocessor 24 records sufficient data pertaining to each sample so that the location or orientation of the sample on the sample plate 16 is recorded. In this manner, microprocessor 24 monitors the location of a sample during the process and is able to associate a sample from a specific sample container with the sample on the sample plate 16. Sample plate 16 and sample container 34 preferably include machine-readable indicia or identifier, such as a bar code, that can be read by a suitable reader or other detector. The reader is operatively connected to microprocessor 24 to monitor the location of the samples throughout the analytical process.

Typically, robotic arm 26 is sequentially operated to move to a position above sample container 34, remove a sample from a selected sample well 46, and then deposit the sample on sample plate 16 while microprocessor 26 records the location to the sample. The process steps are repeated until each sample from sample container 34 is transferred to sample plate 16. In other embodiments, microprocessor 24 is programmed to remove selected samples from sample container 34 based on selected criteria and deposit the selected samples on the sample plate 16. Preferably, microprocessor 24 is programmable so that the operator can program the apparatus to transfer selected samples to sample plate 16 in a predetermined pattern or order.

Figure 3:
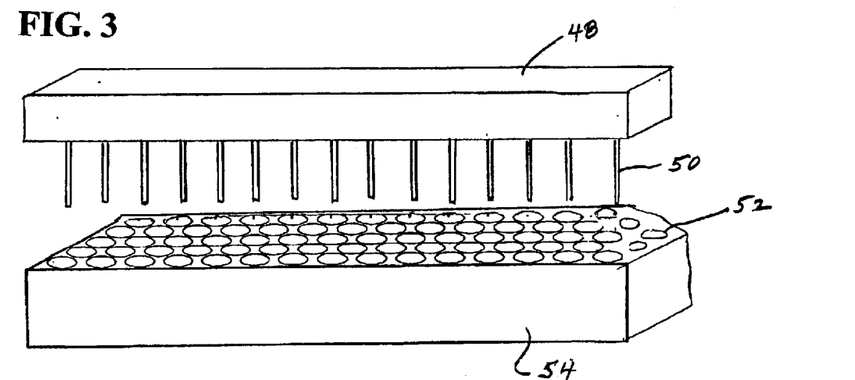
FIG. 3 is a perspective view of an automated multi-pipette system in a second embodiment of the invention.
Figure 3A:
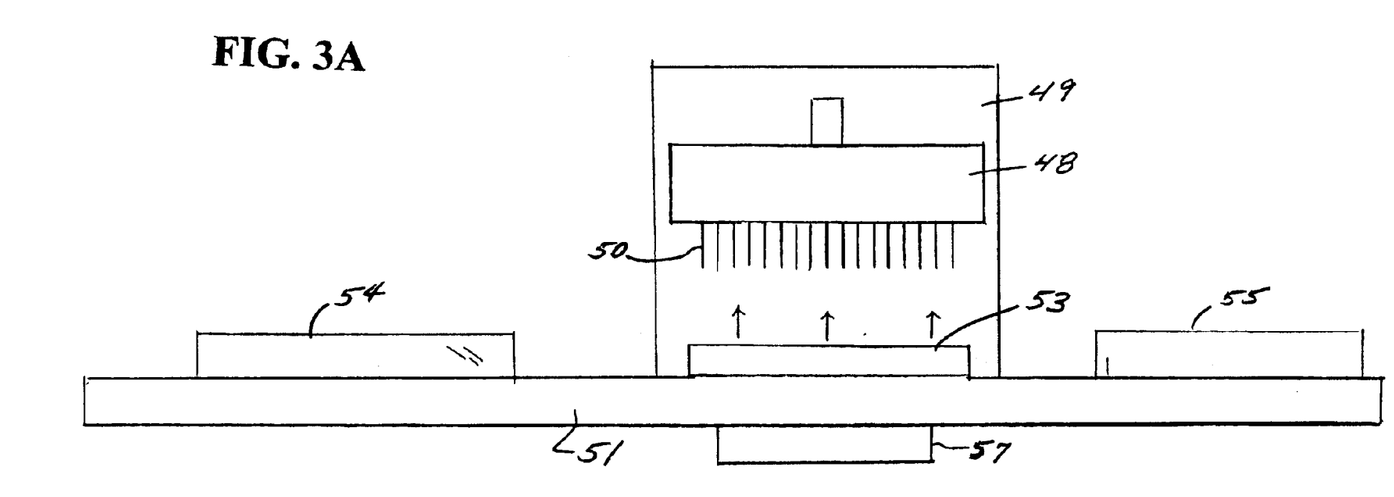
FIG. 3A is a front view of the system of FIG. 3.

FIGS. 3 and 3A show another embodiment of an automated pipetting apparatus. In this embodiment, the pipetting apparatus includes an arm 48 which carries a plurality of pipettes 50. Pipettes 50 are able to simultaneously withdraw a sample from a respective well 52 of a microtiter plate 54 and transfer the samples to a sample plate. As shown in FIG. 3A, arm 48 is mounted on a support 49. A conveyor 51 is positioned below arm 48 for moving a support plate 53 into a position for receiving the liquid samples. A supply container 54, such as a microtiter plate, is provided on the conveyor 51. Conveyor 51 is actuated to move supply container 54 to a position below pipettes 50. In one embodiment, arm 48 lowers pipettes 50 into the wells 52 of supply container 54 to withdraw the sample from the respective well 52 as shown in FIG. 3. Pipettes 50 are withdrawn from the wells 52 and conveyor 51 is actuated to move support plate 53 into the position shown in FIG. 3A. Arm 48 is lowered to a position for dispensing the liquid samples onto the support plate. A wash container 55 can be provided on conveyor 51 and moved into position below the pipettes 50 for washing residue from the inner and outer surfaces of the pipettes. In one preferred embodiment, arm 48 and pipettes 50 are stationary and conveyor 51 includes a lift mechanism 57 for raising the respective container into contact with the pipettes 50 and then lowering the container back to the conveyor 51.

In another embodiment, the automatic pipetting apparatus 10 can include an automated stacking device for handling a large number of microtiter plates and sample plates. A suitable conveyor is included to transport a selected microtiter plate that contains the samples to the automated pipetting assembly where the samples are withdrawn from the microtiter plate and deposited on the sample plate for the mass spectrometer. The microtiter plate is then returned to the stacking device and a new microtiter plate is conveyed to the pipetting apparatus. In a similar manner, the sample plate for the mass spectrometer is filled with the sample spots and conveyed to a stacking device. Preferably, each microtiter plate and sample plate have identifying indicia to coordinate the samples with a sample plate. One example of an automatic pipetting device and stacking device is available under the trademark CyBi-Well.

In preferred embodiments, supply tube 30 and pump 28 contain a pressure transmitting liquid 56 to apply a pressure to the tip of pipette 29 for withdrawing and dispensing a sample. It will be understood that the actuation and operation of pipettes 50 of the embodiment of FIGS. 3 and 3A are substantially the same as the operation of the pipette 29 of the embodiment of FIG. 1. For purposes of explanation, the following description refers to pipette 29 of FIG. 1, although it will be understood that the description is applicable to the multipipetting apparatus of FIGS. 3 and 3A. The pressure transmitting liquid is a non-compressible liquid that can be used to create a suction in pipette 29 for drawing a sample and for dispensing a sample from the pipette. Typically, the pressure transmitting liquid is deionized water, although other non-compressible liquids can be used that do not interfere with the sample.

Figure 4:
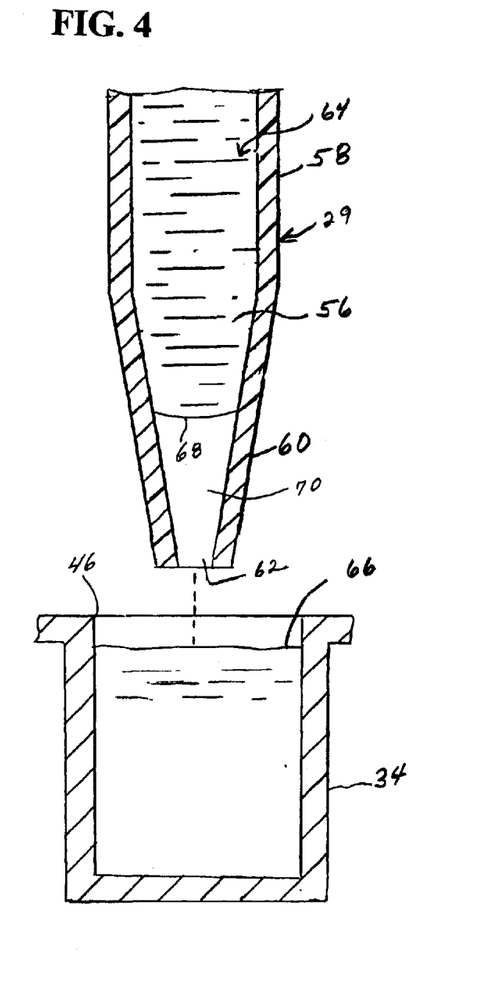
FIG. 4 is a partial cross-sectional side view showing the pipette tip containing a pressure transmitting liquid and air gap where the pipette is in position to capture a liquid sample from a sample container.

In a first embodiment of the invention, the analyte spots are formed on the mass spectrometry sample plate 16 using the automated pipetting apparatus 10. Referring to FIG. 4, pipette 29 containing the pressure transmitting liquid 56 is positioned above a selected well 46 of a microtiter plate 34. As shown in the cross-section of FIG. 4, pipette 29 has a generally cylindrical body 58 having a frustoconical shaped tip 60 with an open axial end 62. Cylindrical body 58 has an axial passage 64 for containing the pressure transmitting liquid 56 and for receiving the sample. Pipette 29 has an upstream end coupled to tube 30 and a downstream end defined by tip 60.

In this embodiment, wells 46 of microtiter plate 34 include a sample 66, such as a liquid sample, containing the analyte to be analyzed, a matrix material and a suitable solvent or carrier. As used herein, the term liquid sample refers to any liquid that is to be pipetted. The liquid sample can include a solvent and a solute. In one embodiment, the liquid sample is a volatile liquid. Pump 38 is initially actuated to move the pressure transmitting liquid 56 within pipette 29 to the position shown in FIG. 4. As shown in FIG. 4, the surface tension of the pressure transmitting liquid 56 and the inner dimension of axial passage 64 form a meniscus 68 and prevent pressure transmitting liquid 56 from flowing outward through open end 62 of pipette 29 by gravity. Preferably, an air space 70 is formed at open end 62 of pipette 29.

Figure 5:
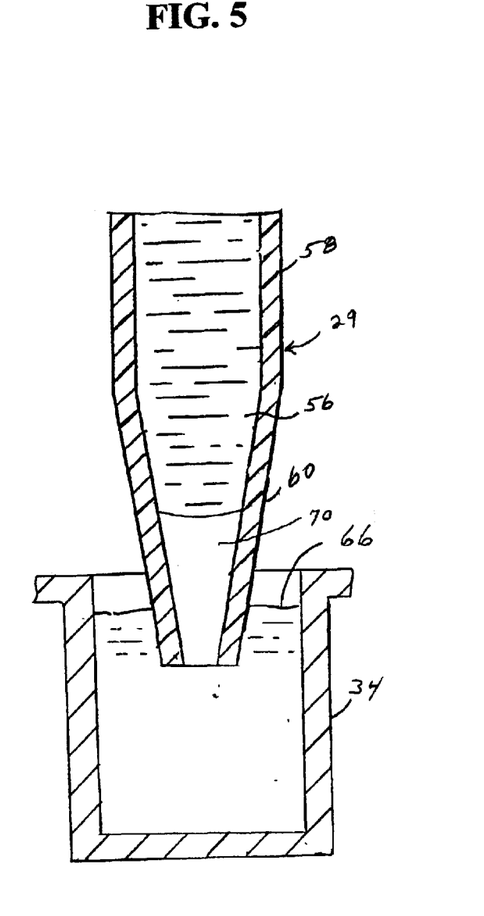
FIG. 5 is a partial cross-sectional view showing the pipette of FIG. 4 immersed in the sample liquid.
Figure 6:
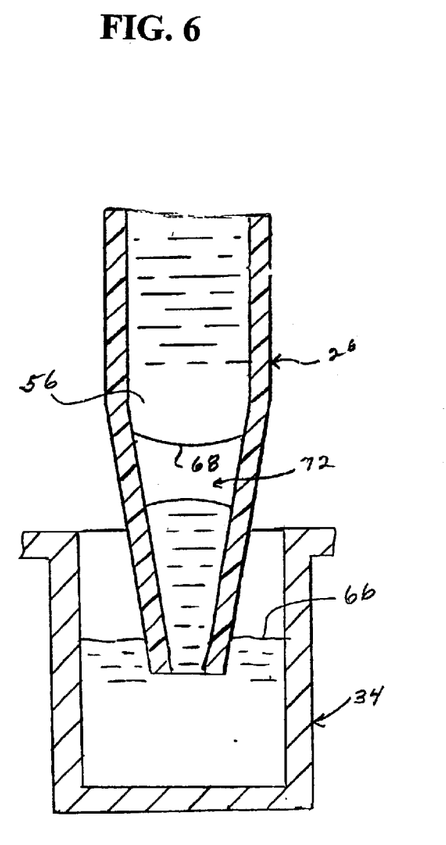
FIG. 6 is a partial cross-sectional view showing the pipette drawing a sample from the sample container and forming an air gap above the liquid sample and the droplet of the liquid sample formed on the tip of the pipette.

Tip 60 of pipette 29 is lowered into sample liquid 66 as shown in FIG. 5. Pump 30 is actuated to draw pressure transmitting liquid 56 upstream, which draws a predetermined volume 74 of sample liquid 66 into pipette 29. Preferably, a pocket or gap 72 of a gaseous material is formed upstream of the volume 74 of the sample liquid and between volume 74 and pressure transmitting liquid 56 as shown in FIG. 6.

Figure 7:
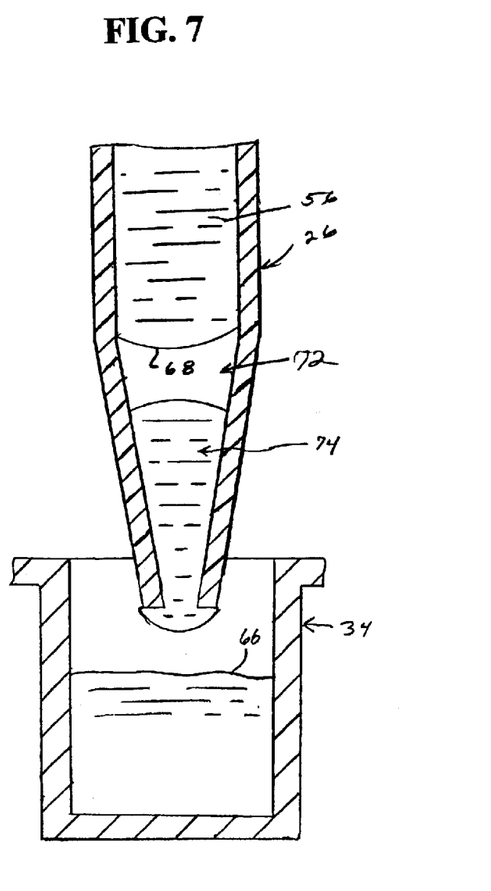
FIG. 7 is a partial cross-sectional view showing the pipette removed from the liquid sample.
Figure 8:
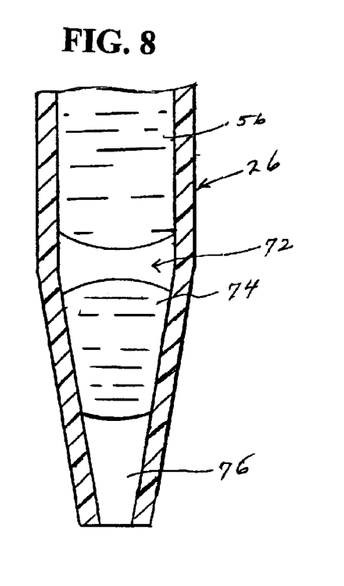
FIG. 8 is a partial cross-sectional view showing the pipette containing a sample where the sample is spaced from the end of the pipette by an air space.
Figure 9:
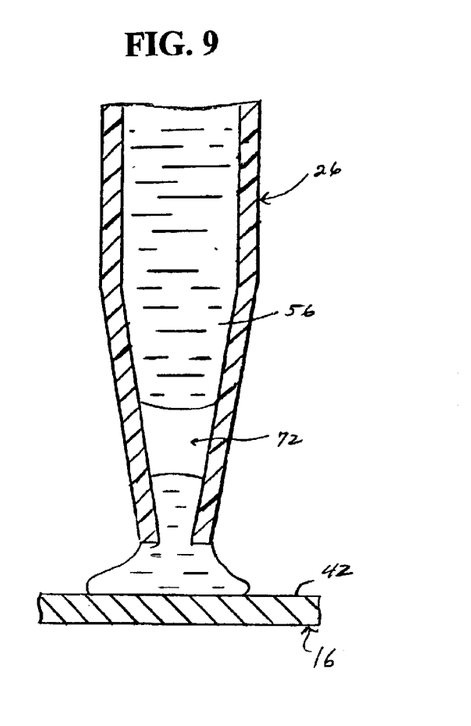
FIG. 9 is a partial cross-sectional view showing the pipette positioned above the support plate and discharging the sample from the pipette.

In one preferred embodiment, pipette 29 is withdrawn from sample liquid 66 while continuously drawing volume 74 of the sample liquid into pipette 29 as shown in FIGS. 7 and 8. Volume 74 of the sample liquid is drawn into pipette 29 a distance to form a layer of a barrier material formed as an air space 76 downstream of volume 74 and to space volume 74 of the sample liquid from open end 62 of pipette 29 as shown in FIG. 8. Preferably, apparatus 10 is operated in a gaseous atmosphere, such as air or an inert or non-reactive gas, which is drawn into pipette 29 to form pocket 72 and space 76. Where an inert or non-reactive gas is to be drawn into the pipette, the apparatus can be enclosed in a suitable housing or containment area. In another embodiment, pump 30 is actuated to draw a predetermined amount of the sample liquid into pipette 29 while pipette 29 is immersed in the liquid. The pump 30 is stopped when the desired volume is drawn into pipette 29 and then pipette 29 is removed from the liquid. Pump 30 is again actuated for a sufficient time to draw volume 74 into pipette 29 and form air space 76.

Air space 76 preferably has a volume sufficient to space the volume 74 of sample liquid from open end 62 of pipette 29 a distance to prevent or inhibit evaporation of the volatile solvents in the sample while the sample is being transferred to the sample plate 16. Preferably, the air space is sufficient to reduce or minimize the evaporation of the volatile liquid so that precise quantities of the volatile liquid can be dispensed without requiring changes in volume caused by the evaporation. In addition, air space 76 spaces the volume 74 of sample liquid from open end 62 a distance sufficient to prevent the sample liquid from flowing outward from the open axial end 62 and being drawn upwardly along the outer surface 78 of pipette 29 by the surface tension of the sample liquid. Preferably, the sample liquid is drawn into pipette 29 a distance so that the air being drawn into pipette 29 to form air space 76 also draws any droplets adhering to outer surface 78 of pipette 29 into axial passage 64 of pipette 29. By drawing the droplets into pipette 29 and preventing the droplets of the sample liquid from adhering to the outer surface 78 of pipette 29, the evaporation of the volatile solvents in the sample liquid is reduced and the deposition of matrix materials on the outer surface 78 is substantially prevented.

Figure 10:
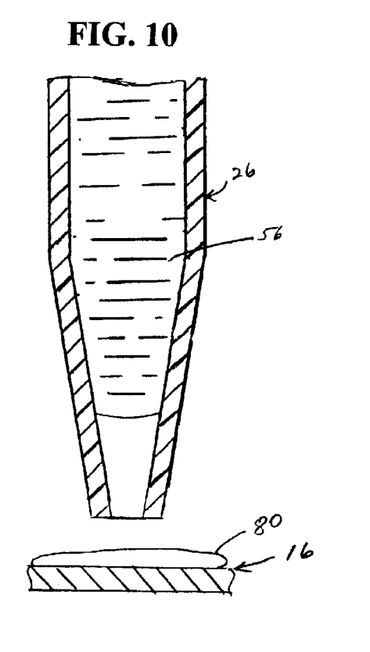
FIG. 10 is a partial cross-sectional view of the pipette after depositing the sample on the support plate.
Figure 11:
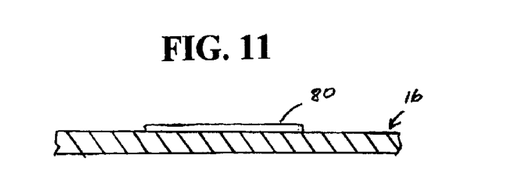
FIG. 11 is a partial cross-sectional view of the support plate showing the dried sample spot.

After the sample is drawn into pipette 29, pipette 29 is then moved to a selected position above sample plate 16 as shown in FIG. 8. The volume 74 of the liquid sample is dispensed onto top surface 42 of plate 16 by actuating pump 28 to produce a positive pressure in pipette 29. Pump 30 pumps the pressure transmitting liquid to apply a dispensing pressure on the air pocket 72 above the sample 74 which forces the sample from pipette 29 onto sample plate 16. In one embodiment, the sample liquid is dispensed completely from the pipette. In alternative embodiments, a portion of the liquid sample is dispensed onto sample plate 16. The portion of the sample remaining in the pipette can be discarded. The liquid sample 74 is then allowed to dry to form a sample spot 80 on sample plate 16 as shown in FIG. 10. Sample plate 16 is then directed to the MALDI mass spectrometer for an analysis of the analytes in the sample spot 80.

Pipette 29 is dimensioned to transfer a suitable volume of a sample liquid from a storage container, such as a microtiter plate, to the sample plate 16. Typically, the volume of the sample liquid is about 0.5 microliter to about 1.5 microliter. Microprocessor 24 coordinates the movement of arm 26 and pump 30 to draw a desired volume of the liquid sample and to draw the air gap into pipette. Microprocessor 24 then actuates drive device 21 and drive mechanism 27 to position pipette 29 of plate 16 and actuates pump 30 to dispense and deposit the liquid sample on the sample plate 16 without discharging the pressure transmitting liquid from pipette 29. The volume of air pocket 72 and air space 76 can vary depending on the composition of the sample liquid and the dimensions of pipette 29. Typically, air pocket 72 and air space 76 have a volume of about 0.5 to about 1.5 microliter. In one preferred embodiment, air pocket 72 and air space 76 have a volume of about 1.0 microliter.

Pump 30 is capable of supplying a dispensing pressure to air pocket 72 to dispense volume 74 of the sample liquid directly onto the surface 42 of sample plate 16 quickly without droplets of the sample liquid adhering to the outer surfaces of pipette 29. Microprocessor 24 can actuate pump 30 so that pressure transmitting liquid 56 discharges the air in air space 76, volume 74 of the sample liquid and the air in air gap 72 toward sample plate 16 with a sufficient burst of force to transfer substantially the entire volume of the sample liquid onto a single spot on sample plate 16 while preventing the liquid from wicking up to outer surface of pipette 29 by the surface tension.

In the embodiment described above, the barrier material drawn into the pipette to space the liquid sample from the tip of the pipette is air. In another embodiment, a volume of air is drawn into the pipette to space the liquid sample from the tip of the pipette followed by a volume of a second barrier material. The second barrier material is preferably a material that is able to form a vapor barrier for the liquid sample to inhibit evaporation of the liquid sample from pipette 29. In one embodiment, the barrier material is selected from the group consisting of liquids, emulsions, slurries and powders. Examples of suitable liquids include mineral oil or other organic liquids that have a low vapor pressure and are not reactive with the sample liquids. In one embodiment, the liquid is immiscible with the liquid being aspirated. Typically, the emulsions and slurries are aqueous emulsions and slurries. Preferably, the barrier material has a vapor pressure less than the vapor pressure of the liquid sample being pipetted. The pipette typically draws a small volume of the barrier material necessary to close to the tip of the pipette and to inhibit evaporation of the liquid sample. The volume of the barrier material can vary depending on the dimensions of the pipette. In one embodiment for pipetting liquid samples of 10 microliters or less, the volume of the barrier material is typically 1 microliter or less provided the tip of the pipette is closed by the barrier material.

Embodiment of FIGS. 11–17

In a second embodiment of the invention, apparatus 10 can be used to form sample spots on a sample plate by a sequence of steps shown in FIGS. 11–17. In this embodiment, the sample containing the analyte is formed with suitable solvents without the use of a matrix material. In one embodiment, the sample liquid contains an analyte dissolved in a mixture of ethanol and acetone. A sample 82 is drawn into a pipette 84 with an air gap 86 formed on the upstream side of sample 82 between sample 82 and pressure transmitting liquid 88. In this embodiment, sample 82 has a volume of about 1.2 microliter and air gap 86 has a volume of about 1.0 microliter. In the embodiment illustrated, sample 82 is drawn into pipette 84 to form an air space 90 between sample 82 and open end 92 of pipette 84. In alternative embodiments, sample 82 can be drawn into pipette 84 without the formation of air space 90.

Figure 12:
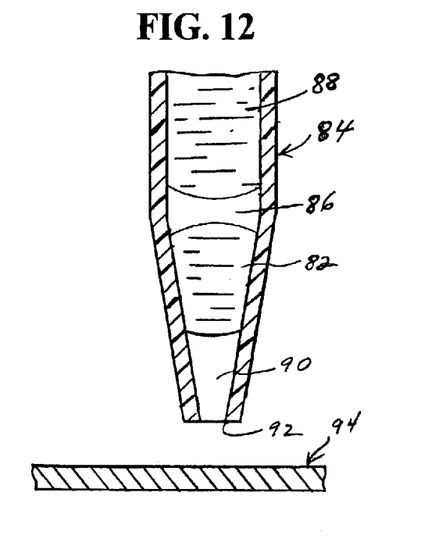
FIG. 12 is a cross-sectional side view of the pipette in a second embodiment of the method for depositing a sample liquid onto a support plate.
Figure 13:
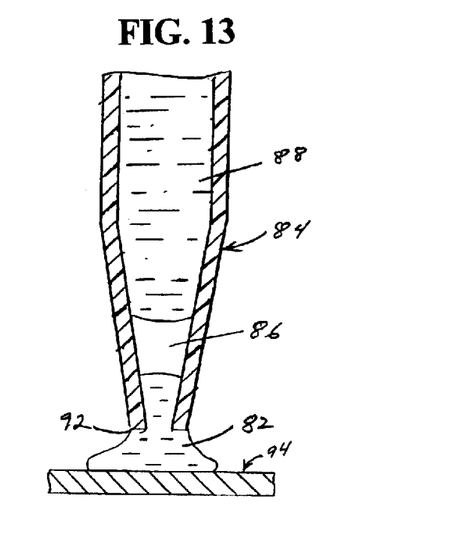
FIG. 13 is a cross-sectional side view of the pipette of FIG. 12 showing the sample being discharged onto the support plate.

Pipette 84 is carried by the automated robotic arm to a position above a sample plate 94 shown in FIG. 12. Sample 84 is then dispensed from pipette 84 onto sample plate 94 as shown in FIG. 13. The process is repeated to form a plurality of sample spots on sample plate 94 as in the previous embodiment.

Figure 14:
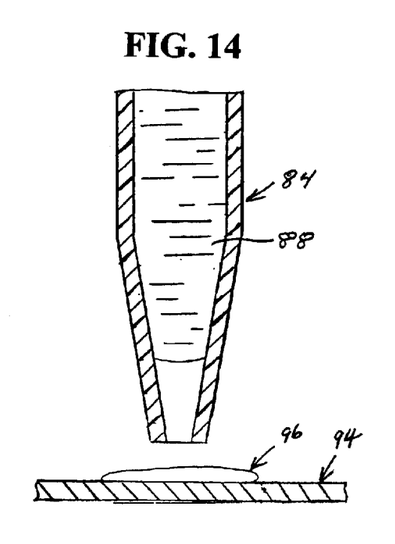
FIG. 14 is a cross-sectional side view of the pipette of FIG. 12 having the sample spot deposited on the support plate.
Figure 15:
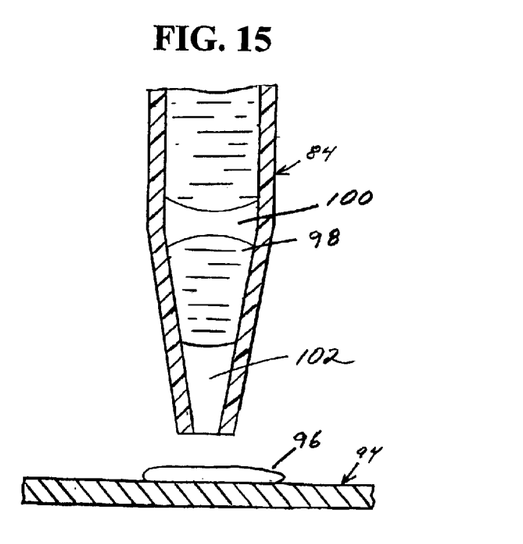
FIG. 15 is a cross-sectional side view of the pipette of FIG. 12 containing a matrix material.
Figure 16:
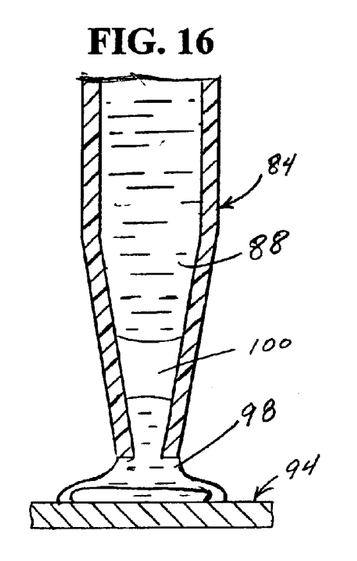
FIG. 16 is a cross-sectional side view of the pipette of FIG. 12 dispensing the matrix material onto the sample spot.

Before the sample droplets 96 on sample plate 94 have dried, a matrix material is deposited directly on top of droplets 96. The matrix material typically contains a highly volatile solvent. Pipette 84 draws a volume 98 of a matrix forming solution for delivering onto sample droplets 96. Preferably, volume 98 of matrix material is drawn into pipette 84 with an air gap 100 between volume 98 and pressure transmitting liquid 88. In addition, an air space 102 is provided between volume 98 and open end 92 of pipette 84 to prevent evaporation of the volatile solvent. In one preferred embodiment, air gap 100 and air space 102 have a volume of about 1.0 microliter. The volume 98 of matrix material in one preferred embodiment has a volume of about 1.6 microliter. Pipette 84 is positioned directly above sample droplet 96 as shown in FIG. 14 and deposited directly onto sample droplet 96 as shown in FIGS. 15 and 16.

Figure 17:
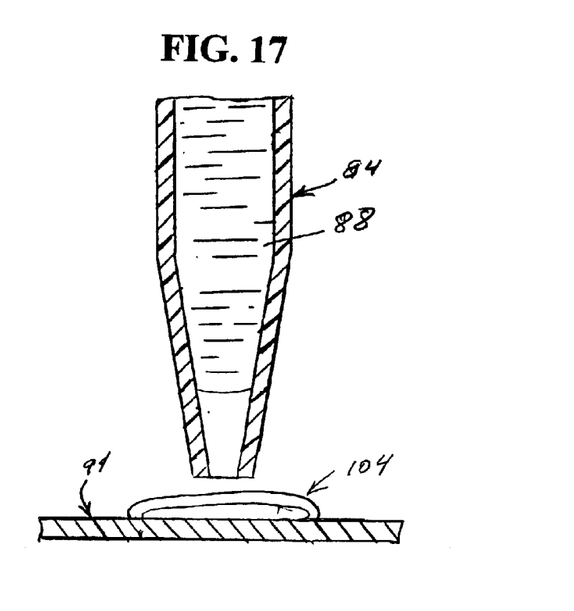
FIG. 17 is a cross-sectional side view of the matrix material deposited onto the sample spot.
Figure 18:
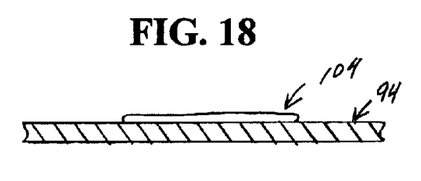
FIG. 18 is a cross-sectional side view of the matrix showing the dried sample spot and matrix material.

Sample droplet 96 and the matrix material are allowed to dry to form a spot 104 on sample plate 94 as shown in FIG. 17. Thereafter, a wash solution such as a 1% aqueous formic acid solution is applied directly to the dried spot 104. After a sufficient period of time to dissolve salts and other impurities, the wash solution is removed. The resulting spot 104 is preferably substantially free of salts and other impurities. The washed sample spot 104 is then recrystallized by depositing a suitable organic solvent using pipette 84.

The organic solvent is preferably drawn into pipette 84 to form an air space between the volume of the organic solvent and the tip of pipette 84 to prevent the solvent from being drawn along the outer surface of the pipette where the solvent will evaporate and leave residues on the outer surface of the pipette. In one preferred embodiment, about 0.7 microliter of a volatile organic solvent capable of recrystallizing the matrix material is dispensed directly onto the sample spot 104. As the solvent evaporates, the matrix material recrystallizes. The samples then can be transferred to the mass spectrometer for analysis.

The method and apparatus of the invention are particularly suitable for transferring small volumes of volatile liquids to reduce the loss of the liquids due to evaporation while transferring the volatile liquids between a storage vessel and a receiving vessel. In the embodiments described herein, it is important to maintain the storage vessel containing the volatile liquid at a temperature to minimize evaporation. In further embodiments, the sample plate can also be cooled to control the rate of evaporation. In the embodiments discussed herein, the automated pipetting apparatus is used for transferring samples containing an analyte to a support plate for a mass spectrometer. In alternative embodiments, the automated pipetting apparatus and method are suitable for transferring samples to other analytical devices for analyzing biological samples.

The invention is described herein in connection with spotting sample plates for use in mass spectrometry analysis of samples. The method and apparatus can also be used for microarray spotting for various processes. In one embodiment, samples can be dispensed onto a support and allowed to dry and/or crystallize. A second substance can then be deposited onto the dried sample and allowed to dry to form various layers on the support.

In a first embodiment of the invention as described above, a pressure transmitting liquid is used to draw in or aspirate the sample and to dispense the liquid sample from the pipette. In other embodiments, the pipette can be used without a pressure transmitting liquid so that air is used to dispense the sample.

In another embodiment of the invention, a pipette or probe partially dispenses the material being transferred by the pipette tip so that a portion of the liquid remains in the pipette tip. In this embodiment, the pipetting device can use a pressure transmitting liquid as in the previous embodiment or the liquid can be aspirated with the use of air only. The method of this embodiment inserts the pipette tip into a vessel containing a liquid to be transferred and draws in an amount of the liquid in excess of the amount to be deposited on the support. The pipette tip is then positioned above the support and a predetermined amount of the sample is dispensed onto the support. The amount of the sample dispensed from the pipette tip onto the support is less than the original amount of the liquid drawn into the pipette tip. Dispensing an amount of the liquid that is less than the amount drawn in reduces the spraying or spattering of the liquid when completely dispensed. The air bubble between the sample and the pressure transmitting liquid can cause the volume of liquid to form bubbles which pop and spatter the last portion of the liquid when dispensed. Similarly, when pressurized air is used to dispense the liquid, the air discharged from the pipette can cause the liquid and particularly small droplets adhering to the pipette tip to spatter onto the support. In addition, the air bubble can pop as the last portion of the liquid is dispensed, thereby causing spattering and contamination of the adjacent sample spots.

In the method of this embodiment, a portion of the liquid that is drawn into the pipette is retained in the pipette after dispensing a predetermined amount of the sample. After the predetermined volume of the sample is deposited on the support, the pipette tip with the remaining portion of the sample contained therein is moved to or positioned above a waste container. The remaining liquid is discharged into the waste container and an amount of air is used to purge the liquid from the pipette. A washing liquid can then be drawn into the pipette tip and discharged to wash the pipette tip for subsequent use. In other embodiments, the pipette can include a disposable tip that is ejected and discarded at the end of the pipetting process. The discarding of the disposable pipette tip can also be carried out with a washing step.

In an illustrative example of the method, the automated pipetting device is programmed to dispense 5 microliters of a liquid onto a support. The pipetting device initially aspirates a volume of 8 microliters of the liquid into the pipette tip. While maintaining the vacuum in the pipette, the pipette tip is removed from the liquid in the storage vessel to aspirate an additional volume of 4 microliters of air into the pipette tip to space the volume of the liquid sample from the tip of the pipette. The pipette is then positioned above the support surface and the pipetting apparatus is programmed to dispense 9 microliters to purge the 4 microliters of air at the tip and to dispense 5 microliters of the liquid sample. The pipette with the remaining 3 microliters of the liquid sample is positioned above a waste container where the remaining liquid sample can be discharged and the pipette purged with air to remove any remaining droplets from the pipette.

While several embodiments of the invention have been described herein, it will be appreciated that various changes and modifications can be made without departing from the scope of the invention as defined in the appended claims.

What is claimed is:

1. A method of depositing a liquid sample onto a support, said method comprising the steps of:

drawing a volume of a liquid sample through an open axial end of a pipette into an axial passage of said pipette;

drawing a volume of a barrier material through said open axial end of said pipette to draw said volume of said liquid sample into said axial passage and to space said volume of liquid sample from said axial end by said volume of said barrier material, where said liquid sample is spaced from said axial end of said pipette a distance to inhibit evaporation of said liquid sample; and positioning said open axial end of said pipette above a target site of said support, expelling said volume of said barrier material from said pipette, and discharging said liquid sample onto said target-site.

2. The method of claim 1, wherein said barrier material is a gas.

3. The method of claim 1, wherein said barrier material is selected from the group consisting of liquids, emulsions, slurries, powders and foams.

4. The method of claim 1, wherein said barrier material is a liquid, emulsion, slurry or foam and said method comprises drawing said volume of liquid sample into said pipette to form an air space and thereafter drawing said barrier material into said pipette.

5. The method of claim 1, comprising depositing a plurality of said liquid samples on said support to form a microarray of sample spots.

6. The method of claim 1, comprising drawing said volume of liquid sample into said axial passage of said pipette a distance from said open axial end to inhibit evaporation of said liquid sample from said pipette.

7. The method of claim 6, comprising drawing said volume of liquid sample into said axial passage a distance to prevent said liquid sample from wicking from said axial passage to an outer surface of said pipette.

8. The method of claim 2, wherein said gas is air.

9. The method of claim 1, comprising drawing said volume of said barrier material into said pipette a distance to substantially prevent leakage and evaporation of said liquid sample from said pipette.

10. The method of claim 2, comprising
positioning said open axial end of said pipette into a vessel containing said liquid sample,
applying a suction to said pipette to draw said volume of liquid sample into said axial passage, and thereafter withdrawing said open axial end from said vessel and drawing said volume of gas into said pipette, and
discontinuing said suction to retain said volume of liquid sample in said pipette.

11. The method of claim 1, wherein said pipette contains a pressure transmitting liquid for drawing and dispensing said liquid sample from said pipette.

12. The method of claim 1, wherein said liquid sample contains a volatile solvent or carrier.

13. The method of claim 1, wherein said liquid sample has a vapor pressure of at least about 3.5 kPa at 25° C.

14. The method of claim 1, wherein said volume of said barrier material is an amount sufficient to inhibit evaporation of said liquid sample from said pipette.

15. The method of claim 1, wherein said volume of said liquid sample is about 2 ml or less.

16. The method of claim 1, wherein said volume of said liquid sample is about 10 microliters or less.

17. The method of claim 1, comprising providing a plurality of said pipettes and simultaneously drawing a volume of said liquid samples into said pipettes followed by drawing a volume of said barrier material, and discharging said samples onto said support to form a microarray of sample spots.

18. A method of loading a liquid material onto a mass spectrometer plate, said method comprising the steps of:
drawing a volume of a liquid material into a pipette and drawing a volume of a barrier material into said pipette to space said volume of said liquid sample from an outlet end of said pipette to inhibit loss of said liquid material from said pipette;
positioning said pipette in a dispensing location with respect to a mass spectrometer plate while retaining said volume of said liquid sample completely within said pipette; and
discharging said barrier material and at least a portion of said volume of said liquid sample from said pipette and depositing said liquid sample onto a target site on said plate.

19. The method of claim 18, wherein said barrier material is air and said method comprises discharging said volume of said liquid sample completely from said pipette.

20. The method of claim 18, wherein said liquid material is a volatile liquid, and said method comprises drawing said volume of said barrier material into said pipette to space said volume of said liquid sample from said outlet end of said pipette a distance to inhibit evaporation of said liquid sample from said pipette.

21. The method of claim 20, comprising drawing said volume of said barrier material into said pipette to space said volume of said liquid sample from said outlet end of said pipette to inhibit wicking of said liquid sample onto an outer surface of said pipette.

22. The method of claim 18, wherein said liquid sample contains a solvent or carrier that is volatile at room temperature and atmospheric pressure.

23. The method of claim 19, comprising
positioning said outlet end of said pipette in a vessel containing said liquid sample,
applying a suction to said pipette to draw said volume of said liquid sample into said pipette and withdrawing said pipette from said liquid sample in said vessel while continuing said suction to draw said volume of air into said pipette, and
thereafter discontinuing said suction and retaining said volume of liquid in said pipette.

24. The method of claim 18, wherein said pipette contains a pressure transmitting liquid for drawing said liquid sample into said pipette and discharging said liquid sample from said pipette.

25. The method of claim 18, wherein said volume of liquid sample is about 0.5 microliters to about 1.5 microliters.

26. The method of claim 25, wherein said volume of said barrier material is about 0.5 microliters to about 1.5 microliters.

27. The method of claim 18, comprising the step of applying a dispensing pressure to said pipette to discharge said liquid sample from said pipette.

28. The method of claim 18, wherein said liquid sample has a vapor pressure of at least about 3.5 kPa at 25° C.

29. The method of claim 18, wherein said pipette is a micropipette and said volume of said liquid material is about 10 microliters or less.

30. The method of claim 18, wherein said mass spectrometer plate is a MALDI mass spectrometer plate.

31. The method of claim 18, wherein said barrier material is selected from the group consisting of liquids, emulsions, slurries, powders and foams, and wherein said method comprises drawing said liquid material into said pipette a distance to form an air space between said liquid material and thereafter drawing said barrier material into said pipette.

32. The method of claim 18, wherein said barrier material is mineral oil.

33. A method of loading a sample onto a mass spectrometer plate, said method comprising the steps of:
inserting an open axial end of a pipette into a liquid sample supply, said pipette having an axial passage in communication with said open axial end;
drawing a volume of said liquid sample into said axial passage;
removing said open axial end of said pipette from said liquid sample supply and drawing a volume of a barrier material into said pipette through said open axial end to space said volume of said liquid sample from said open axial end of said pipette a distance to inhibit evaporation of said liquid sample from said pipette and to prevent wicking of said liquid sample onto an outer surface of said pipette caused by surface tension; and positioning said open axial end of said pipette over a target site on a mass spectrometer plate and discharging said barrier material and said volume of said liquid sample from said pipette to load said volume of said liquid sample on said target site on said mass spectrometer plate.

34. The method of claim 33, wherein said barrier material is air and said method comprises the step of applying a suction to said pipette to draw said volume of liquid and said volume of air into said pipette.

35. The method of claim 33, comprising applying a dispensing pressure to said pipette to discharge said liquid sample from said pipette.

36. The method of claim 34, comprising maintaining said suction while removing said open end of said pipette from said liquid sample to draw said volume of air into said pipette and thereafter discontinuing said suction.

37. The method of claim 33, wherein said liquid sample contains a volatile liquid and has a vapor pressure of greater than about 3.5 kPa at 25° C.

38. The method of claim 33, wherein said pipette contains a pressure transmitting liquid for drawing and dispensing said liquid sample.

39. The method of claim 38, comprising applying a suction to draw said pressure transmitting liquid into said pipette and to draw an air space into said pipette before drawing said liquid sample.

40. The method of claim 33, wherein said barrier material is a liquid having a vapor pressure less than a vapor pressure of said liquid sample.

41. The method of claim 33, wherein said barrier material is air and is drawn into said pipette to form said air pocket having a volume sufficient to inhibit evaporation of said liquid sample from said pipette.

* * * * *